United States Patent
Ge et al.

(10) Patent No.: US 6,436,932 B1
(45) Date of Patent: Aug. 20, 2002

(54) AMINOALKYL SUBSTITUTED PYRROLO[3,2-E] PYRIDINE AND PYRROLO [2,3-B]PYRIMIDINE DERIVATIVES: MODULATORS OF CRF1 RECEPTORS

(75) Inventors: Ping Ge, Branford; Raymond F. Horvath, North Branford; Stephane De Lombaert, Madison, all of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/947,045

(22) Filed: Sep. 4, 2001

Related U.S. Application Data

(62) Division of application No. 09/283,410, filed on Apr. 1, 1999, now Pat. No. 6,310,063.
(60) Provisional application No. 60/080,434, filed on Apr. 2, 1998.

(51) Int. Cl.[7] ............... A61K 31/519; A61K 31/5377; C07D 487/04
(52) U.S. Cl. ................ 514/234.5; 514/258; 544/117; 544/280
(58) Field of Search ............... 544/280, 117; 514/234.5, 258

(56) References Cited

U.S. PATENT DOCUMENTS 6,310,063 B1 * 10/2001 Ge et al. ............... 514/234.5

FOREIGN PATENT DOCUMENTS

WO            94/13676    *   6/1994

OTHER PUBLICATIONS

Mitchell, Neuroscience and Biobehavioral Reviews, vol. 22,pp. 635–651 (1998).*
Dieterich et al. Exp.Clin. Endocrinol. Diabetes ,105,pp. 65–82 (1997).*
Bremner et al. Am. J. Psychiatry,154, pp. 624–629(1997).*

* cited by examiner

*Primary Examiner*—Emily Bernhardt
(74) *Attorney, Agent, or Firm*—McDonnell Boehnen Hulbert & Berghoff

(57) ABSTRACT

Disclosed are compounds of the formula:

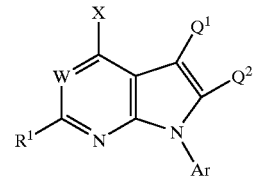

wherein Ar, $Q^1$, $Q^2$, $R^1$, W and X are substituents as defined herein, which compounds are water-soluble $CRF_1$ receptor antagonists, and are therefore useful for the treatment of psychiatric disorders and neurological diseases, including major depression, anxiety-related disorders, post-traumatic stress disorder, supranuclear palsy and feeding disorders, as well as treatment of immunological, cardiovascular or heart-related diseases and colonic hypersensitivity associated with psychopathological disturbance and stress.

18 Claims, No Drawings

AMINOALKYL SUBSTITUTED PYRROLO[3,2-E] PYRIDINE AND PYRROLO [2,3-B]PYRIMIDINE DERIVATIVES: MODULATORS OF CRF1 RECEPTORS

This is a division of application Ser. No. 09/283,410, filed Apr. 1, 1999, which claims priority from application Serial No. 60/080,434, filed Apr. 2, 1998.

BACKGROUND OF THE INVENTION

1. Field of the Invention

The present invention relates to aminoalkyl substituted pyrrolo[3,2-e]pyridine and pyrrolo[2,3-b]pyrimidine derivatives, pharmaceutical compositions containing such compounds, and their use for the treatment of psychiatric disorders and neurological diseases, including major depression, anxiety-related disorders, post-traumatic stress disorder, supranuclear palsy and feeding disorders, as well as treatment of immunological, cardiovascular or heart-related diseases and colonic hypersensitivity associated with psychopathological disturbance and stress.

2. Description of the Related Art

Corticotropin releasing factor (herein referred to as CRF), a 41 amino acid peptide, is the primary physiological regulator of proopiomelanocortin (POMC) derived peptide secretion from the anterior pituitary gland [J. Rivier et al., Proc. Nat. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response of the immune system to physiological, psychological, and immunological stressors [J. E. Blalock, Physiological Reviews 69:1 (1989); J. E. Morley, Life Sci. 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, Hosp. Practice 23:59 (1988)].

In affective disorder, or major depression, the concentration of CRF is significantly increased in the cerebral spinal fluid (CSF) of drug-free individuals [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol Psychiatry 25:355 (1989). Furthermore, the density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (i.v. administered) observed in depressed patients [P. W. Gold et al., Am J. Psychiatry 141:619 (1984); F. Holsboer et al., Psychoneuroendocrinology 9:147(1984); P. W. Gold et al., New Eng. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is preliminary evidence that tricyclic antidepressants can alter CRF levels and thus modulate the numbers of CRF receptors in brain [Grigoriadis et al., Neuropsychopharmacology 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., Life Sci. 31:363 (1982); C. W. Berridge and A. J. Dunn Regul. Peptides 16:83 (1986)]. Preliminary studies using the putative CRF receptor antagonist α-helical ovine CRF (9-41) in a variety of behavioral paradigms demonstrate that the antagonist produces "anxiolytic-like" effects that are qualitatively similar to the benzodiazepines [C. W Berridge and A. J. Dunn Horm. Behav. 21:393 (1987), Brain Research Reviews 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist (Ro 15-1788), which was without behavioral activity alone in the operant conflict test, reversed the effects of CRF in a dose-dependent manner while the benzodiazepine inverse agonist (FG 7142) enhanced the actions of CRF [K. T. Britton et al., Psychopharmacology 94:306 (1988)].

It has been further postulated that CRF has a role in immunological, cardiovascular or heart-related diseases such as hypertension, tachycardia and congestive heart failure, stroke and osteoporosis. CRF has also been implicated in premature birth, psychosocial dwarfism, stress-induced fever, ulcer, diarrhea, post-operative ileus and colonic hypersensitivity associated with psychopathological disturbance and stress.

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (α-helical $CRF_{9-41}$) in a variety of behavioral paradigms have demonstrated that the CRF antagonist produces "anxiolytic-like" effects qualitatively similar to the benzodiazepines [for review see G. F. Koob and K. T. Britton, In: Corticotropin-Releasing Factor: Basic and Clinical Studies of a Neuropeptide, E. B. De Souza and C. B Nemeroff eds., CRC Press p221 (1990)].

SUMMARY OF THE INVENTION

In one aspect, the present invention provides novel compounds which bind to corticotropin releasing factor receptors, thereby altering the anxiogenic effects of CRF secretion. The compounds of the present invention are useful for the treatment of psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in mammals. According to another aspect, the present invention provides novel compounds of Formula I (described below) which are useful as antagonists of the corticotropin releasing factor. The compounds of the present invention exhibit activity as corticotropin releasing factor antagonists and appear to suppress CRF hypersecretion. The present invention also includes pharmaceutical compositions containing such compounds of Formula I, and methods of using such compounds for the suppression of CRF hypersecretion, and/or for the treatment of anxiogenic disorders.

In another aspect, the present invention provides novel compounds, pharmaceutical compositions and methods which may be used in the treatment of affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzbeimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADR); obesity; infertility; head traumas; spinal cord trauma; ischemic neuronal damage (e.g., cerebral ischemia such as cerebral hippocampal ischemia); excitotoxic neuronal damage; epilepsy; cardiovascular and heart related disorders including hypertension, tachycardia and congestive heart failure; stroke; immune dysfunctions including stress induced immune dysfunctions (e.g., stress induced fevers in humans and the following animal diseases: porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in mammals.

In a further aspect of the invention, the compounds provided by this invention (and especially radiolabeled compounds of this invention) are also useful as standards and reagents in determining the ability of a potential pharmaceutical to bind to the $CRF_1$ receptor.

The novel compounds encompassed by the instant invention can be described by general Formula I:

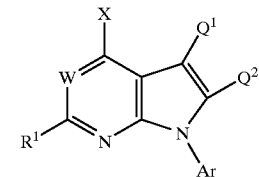

wherein
Ar is phenyl, 1- or 2-naphthyl, 2-, 3-, or 4-pyridyl, 2-, 4- or 5-pyrimidinyl, optionally mono-, di-, or tri-substituted with halogen, trifluoromethyl, hydroxy, amino, lower alkylamino, lower dialkylamino, carboxamido, lower alkylcarboxamido, N,N-lower dialkylcarboxamido, lower alkyl, lower alkoxy, with the proviso that at least one of the positions ortho or para to the point of attachment of Ar to the tricyclic ring system is substituted;

$R^1$ is hydrogen, halogen, trifluoromethyl, lower alkyl, or $(C_1-C_6$ alkyl$)-G^1-R^2$ where $G^1$ is oxygen or sulfur and $R^2$ is hydrogen or $C_1-C_6$ alkyl;

W is N or C—$R^3$ where $R^3$ is hydrogen or lower alkyl;

$Q^1$ is hydrogen, lower alkyl, halogen, lower alkoxy, amino, methylamino, dimethylamino, hydroxymethyl, or $SO_n(C_1-C_4$ alkyl) where n is 0, 1 or 2, cyano, hydroxy, —C(O) $(C_1-C_4$ alkyl), —CHO, —$CO_2$ $(C_1-C_4$ alkyl), —$CO_2(C_1-C_4$ alkenyl), or —$CO_2$ $(C_1-C_4$ alkynyl);

$Q^2$ is hydrogen, lower alkyl, halogen, hydroxymethyl, methoxymethyl, or lower alkoxy;

X is

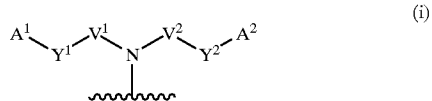

wherein
$V^1$ and $V^2$ are $CH_2$, CO, CS, $SO_2$ or CH(lower alkyl), with the proviso that both $V^1$ and $V^2$ cannot both be CO, CS or $SO_2$;

$Y^1$ and $Y^2$ independently represent a bond or lower alkylene;

$A^1$ is $NR^4R^5$ wherein $R^4$ and $R^5$ are independently hydrogen or a lower alkyl group which optionally forms a heterocycloalkyl group with $Y^1$;

lower alkanoyl, lower alkylsulfonyl, with the proviso that $R^4$ and $R^5$ cannot both be alkanoyl or alkylsulfonyl; or $NR^4R^5$ taken together form a $C_3-C_6$ heterocycloalkyl or a group of the formula:

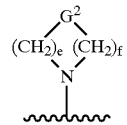

wherein e and f are independently 1, 2 or 3 and the sum of e and f is at least 3; and $G^2$ is
$NR^6$ wherein $R^6$ is hydrogen or lower alkyl, or
$CH(C_0-C_6$ alkylene)—$G^3$—$R^7$ wherein $G^3$ is CONH, CONH(lower alkyl), NH, NH(lower alkyl) and $R^7$ is hydrogen or lower alkyl; or CONH$_2$, CO[N(lower alkyl)R$^8$] wherein R$^8$ is hydrogen or lower alkyl;

A$^2$ is hydrogen, lower alkyl, (C$_1$–C$_6$ alkylene)—G$^4$—R$^9$ wherein G$^4$ is oxygen or sulfur and R$^9$ is hydrogen, trifluoromethyl or lower alkyl;

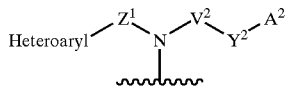

(ii)

wherein heteroaryl is 2-, 3- or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4 pyrazolyl, 1-, 3- or 4-triazolyl, 2-pyrazinyl, or 1-, 2- or 5-tetrazolyl, each of which is optionally mono- or disubstituted with halogen, trifluoromethyl, amino, lower alkyl, lower alkoxy, with the proviso that tetrazolyl can have at most one substituent;

Z$^1$ is lower alkyl; and

V$^2$, Y$^2$ and A$^2$ are as defined above;

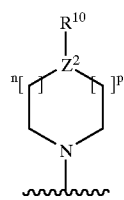

(iii)

where

Z$^2$ is carbon or nitrogen;
where
when Z$^2$ is CH, n is 0, 1, 2 or 3 and p is 1, 2, or 3, R$^{10}$ is carboxamido, or (lower alkylene)-G$^5$—R$^{11}$ wherein G$^5$ is NH, NH(lower alkyl) and R$^{11}$ is hydrogen or lower alkyl;
when Z$^2$ is carbon, n is 1 or 2 and p is 1 or 2, R$^{10}$ is amino; or
when Z$^2$ is nitrogen, n is 1 or 2 and p is 1 or 2, R$^{10}$ is hydrogen; or (iv) a nitrogen heterocycle of the formula:

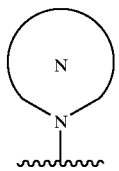

wherein the N-ring represents triazolyl, tetrazolyl, imidazolyl, or pyrazolyl, each of which is optionally substituted with amino, trifluoromethyl, carboxamido, or (lower alkylene)-G$^6$—R$^{12}$ wherein G$^6$ is NH, NH(lower alkyl) and R$^{12}$ is hydrogen or lower alkyl.

The compounds of Formula I are antagonists at the. CRF$_1$ receptor and are useful in the diagnosis and treatment of stress related disorders such as post traumatic stress disorder (PTSD) as well as depression, headache and anxiety.

DETAILED DESCRIPTION OF THE INVENTION

The novel compounds encompassed by the instant invention can be described by general Formula I:

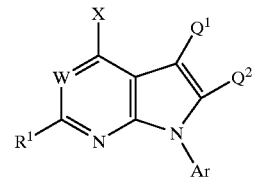

I wherein

Ar is phenyl, 1- or 2-naphthyl, 2-, 3-, or 4-pyridyl, 2-, 4- or 5-pyrimidinyl, optionally mono-, di-, or tri-substituted with halogen, trifluoromethyl, hydroxy, amino, lower alkylamino, lower dialkylamino, carboxamido, lower alkylcarboxamido, N,N-lower dialkylcarboxamido, lower alkyl, lower alkoxy, with the proviso that at least one of the positions ortho or para to the point of attachment of Ar to the tricyclic ring system is substituted;

R$^1$ is hydrogen, halogen, trifluoromethyl, lower alkyl, or (C$_1$–C$_6$ alkyl)-G$^1$—R$^2$ where G$^1$ is oxygen or sulfur and R$^2$ is hydrogen or C$_1$–C$_6$ alkyl;

W is N or C—R$^3$ where R$^3$ is hydrogen or lower alkyl;

Q$^1$ is hydrogen, lower alkyl, halogen, lower alkoxy, amino, methylamino, dimethylamino, hydroxymethyl, or SO$_n$(C$_1$–C$_4$ alkyl) where n is 0, 1 or 2, cyano, hydroxy, —C(O) (C$_1$–C$_4$ alkyl), —CHO, —CO$_2$ (C$_1$–C$_4$ alkyl), —CO$_2$(C$_1$–C$_4$ alkenyl), or —CO$_2$ (C$_1$–C$_4$ alkynyl);

Q$^2$ is hydrogen, lower alkyl, halogen, hydroxymethyl, methoxymethyl, or lower alkoxy;

X is

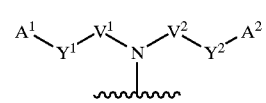

(i)

wherein

V$^1$ and V$^2$ are CH$_2$, CO, CS, SO$_2$ or CH(lower alkyl), with the proviso that both V$^1$ and V$^2$ cannot both be CO, CS or SO$_2$;

Y$^1$ and Y$^2$ independently represent a bond or lower alkylene;

A$^1$ is NR$^4$R$^5$ wherein R$^4$ and R$^5$ are independently hydrogen or a lower alkyl group which optionally forms a heterocycloalkyl group with Y$^1$;

lower alkanoyl, lower alkylsulfonyl, with the proviso that R$^4$ and R$^5$ cannot both be alkanoyl or alkylsulfonyl; or NR$^4$R$^5$ taken together form a C$_3$–C$_6$ heterocycloalkyl or a group of the formula:

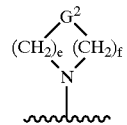

wherein e and f are independently 1, 2 or 3 and the sum of e and f is at least 3; and G$^2$ is
NR$^6$ wherein R$^6$ is hydrogen or lower alkyl, or
CH(C$_0$–C$_6$ alkylene)-G$^3$—R$^7$ wherein G$^3$ is CONH, CONH(lower alkyl), NH, NH(lower alkyl) and R$^7$ is hydrogen or lower alkyl; or CONH$_2$, CO[N(lower alkyl)R$^8$] wherein R$^8$ is hydrogen or lower alkyl;

A$^2$ is hydrogen, lower alkyl, (C$_1$-C$_6$ alkylene)-G$^4$—R$^9$ wherein G$^4$ is oxygen or sulfur and R$^9$ is hydrogen, trifluoromethyl or lower alkyl;

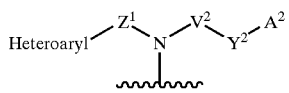

(ii)

wherein heteroaryl is 2-, 3- or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono- or disubstituted with halogen, trifluoromethyl, amino, lower alkyl, lower alkoxy, with the proviso that tetrazolyl can have at most one substituent;

Z$^1$ is lower alkyl; and

V$^2$, Y$^2$ and A$^2$ are as defined above;

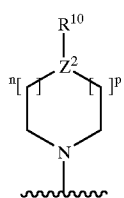

(iii)

where

Z$^2$ is carbon or nitrogen;

where when Z$^2$ is CH, n is 0, 1, 2 or 3 and p is 1, 2, or 3, R$^{10}$ is carboxamido, or (lower alkylene)-G$^5$—R$^{11}$ wherein G$^5$ is NH, NH(lower alkyl) and R$^{11}$ is hydrogen or lower alkyl;

when Z$^2$ is carbon, n is 1 or 2 and p is 1 or 2, R$^{10}$ is amino; or when Z$^2$ is nitrogen, n is 1 or 2 and p is 1 or 2, R$^{10}$ is hydrogen; or (iv) a nitrogen heterocycle of the formula:

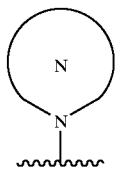

wherein the N-ring represents triazolyl, tetrazolyl, imidazolyl, or pyrazolyl, each of which is optionally substituted with amino, trifluoromethyl, carboxamido, or (lower alkylene)-G$^6$—R$^{12}$ wherein G$^6$ is NH, NH(lower alkyl) and R$^{12}$ is hydrogen or lower alkyl.

Preferred compounds of the invention have formula II:

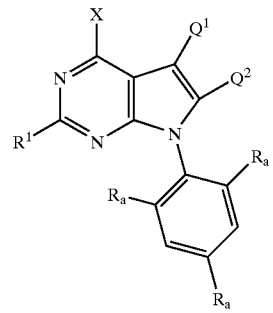

II wherein each R$_a$ independently represents lower alkyl;

Ar is phenyl, 1- or 2-naphthyl, 2-, 3-, or 4-pyridyl, 2-, 4- or 5-pyrimidinyl, optionally mono-, di-, or tri-substituted with halogen, trifluoromethyl, hydroxy, amino, lower alkylamino, lower dialkylamino, carboxamido, lower alkylcarboxamido, N,N-lower dialkylcarboxamido, lower alkyl, lower alkoxy, with the proviso that at least one of the positions ortho or para to the point of attachment of Ar to the tricyclic ring system is substituted;

R$^1$ is hydrogen, halogen, trifluoromethyl, lower alkyl, or (C$_1$-C$_6$ alkyl)-G$^1$—R$^2$ where G$^1$ is oxygen or sulfur and R$^2$ is hydrogen or C$_1$-C$_6$ alkyl;

W is N or C—R$^3$ where R$^3$ is hydrogen or lower alkyl;

Q$^1$ is hydrogen, lower alkyl, halogen, lower alkoxy, amino, methylamino, dimethylamino, hydroxymethyl, or SO$_n$(C$_1$-C$_4$ alkyl) where n is 0, 1 or 2, cyano, hydroxy, —C(O) (C$_1$-C$_4$ alkyl), —CHO, —CO$_2$ (C$_1$-C$_4$ alkyl), —CO$_2$(C$_1$-C$_4$ alkenyl), or —CO$_2$ (C$_1$-C$_4$ alkynyl);

Q$^2$ is hydrogen, lower alkyl, halogen, hydroxymethyl, methoxymethyl, or lower alkoxy;

X is

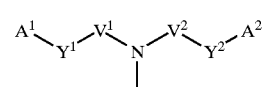

(i)

wherein

V$^1$ and V$^2$ are CH$_2$, CO, CS, SO$_2$ or CH(lower alkyl), with the proviso that both V$^1$ and V$^2$ cannot both be CO, CS or SO$_2$;

Y$^1$ and Y$^2$ independently represent a bond or lower alkylene;

A$^1$ is NR$^4$R$^5$ wherein R$^4$ and R$^5$ are independently hydrogen or a lower alkyl group which optionally forms a heterocycloalkyl group with Y$^1$;

lower alkanoyl, lower alkylsulfonyl, with the proviso that R$^4$ and R$^5$ cannot both be alkanoyl or alkylsulfonyl; or NR$^4$R$^5$ taken together form a C$_3$-C$_6$ heterocycloalkyl or a group of the formula:

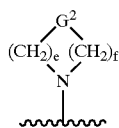

wherein e and f are independently 1, 2 or 3 and the sum of e and f is at least 3; and $G^2$ is $NR^6$ wherein $R^6$ is hydrogen or lower alkyl, or $CH(C_0$–$C_6$ alkylene)-$G^3$—$R^7$ wherein $G^3$ is CONH, CONH(lower alkyl), NH, NH(lower alkyl) and $R^7$ is hydrogen or lower alkyl; or $CONH_2$, CO[N(lower alkyl)$R^8$] wherein $R^8$ is hydrogen or lower alkyl;

$A^2$ is hydrogen, lower alkyl, ($C_1$–$C_6$ alkylene)-$G^4$—$R^9$ wherein $G^4$ is oxygen or sulfur and $R^9$ is hydrogen, trifluoromethyl or lower alkyl;

(ii)

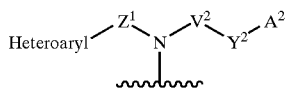

wherein heteroaryl is 2-, 3- or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono- or disubstituted with halogen, trifluoromethyl, amino, lower alkyl, lower alkoxy, with the proviso that tetrazolyl can have at most one substituent;

$Z^1$ is lower alkyl; and $V^2$, $Y^2$ and $A^2$ are as defined above;

(iii)

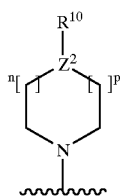

where $Z^2$ is carbon or nitrogen;

where when $Z^2$ is CH, n is 0, 1, 2 or 3 and p is 1, 2, or 3, $R^{10}$ is carboxamido, or (lower alkylene)-$G^5$—$R^{11}$ wherein $G^5$ is NH, NH(lower alkyl) and $R^{11}$ is hydrogen or lower alkyl;

when $Z^2$ is carbon, n is 1 or 2 and p is 1 or 2, $R^{10}$ is amino; or when $Z^2$ is nitrogen, n is 1 or 2 and p is 1 or 2, $R^{10}$ is hydrogen; or (iv) a nitrogen heterocycle of the formula:

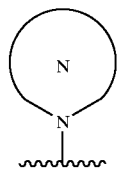

wherein the N-ring represents triazolyl, tetrazolyl, imidazolyl, or pyrazolyl, each of which is optionally substituted with amino, trifluoromethyl, carboxamido, or (lower alkylene)-$G^6$—$R^{12}$ wherein $G^6$ is NH, NH(lower alkyl) and $R^{12}$ is hydrogen or lower alkyl.

In Formula II, $Q^1$ and $Q^2$ preferably independently represent hydrogen, methyl, or ethyl. More preferred compounds of Formula II are those where N—$V^2$—$Y^2$—$A^2$ represents N-cyclopropylmethyl. Other more preferred compounds of Formula II include those where one of $Q^1$ and $Q^2$ is methyl or ethyl and the other is hydrogen.

Still other more preferred compounds of Formula II are those where N—$V^2$—$Y^2$—$A^2$ represents N-cyclopropylmethyl, $Q^1$ is methyl or ethyl, and —$V^1$—$Y^1$—$A^1$ represents

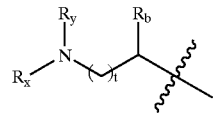

hereinafter Formula II-a, wherein $R_b$ is hydrogen or methyl;

t is 1, 2 or 3, more preferably 1;

$R_x$ is hydrogen, $C_1$–$C_6$ alkyl, phenyl($C_1$–$C_6$)alkyl where phenyl is optionally mono- or disubstituted independently with $C_1$–$C_6$ alkyl, $C_1$–$C_6$ alkoxy, halogen, or hydroxy; and $R_y$ is hydrogen, $C_1$–$C_6$ alkyl, ($C_3$–$C_6$)cycloalkyl; or $NR_xR_y$ represents pyrrolidinyl, N-($C_1$–$C_6$) alkylpyrrolidin-2-yl, piperidinyl, morpholinyl, or N-($C_1$–$C_6$)alkylpiperazinyl.

Particularly preferred compounds of Formula II include those where N—$V^2$—$Y^2$—$A^2$ represents N-cyclopropylmethyl, $Q^1$ is methyl, and —$V^1$—$Y^1$—$A^1$ represents II-a where $R_b$ is hydrogen, and t is 1. Particularly preferred $R_x$ and $R_y$ groups are independently hydrogen or $C_1$–$C_2$ alkyl, or where $NR_xR_y$ represents pyrrolidinyl, piperidinyl or piperazinyl.

Other preferred compounds of the invention have formula III:

III

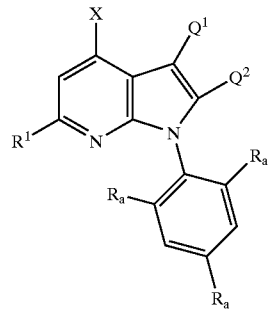

wherein each $R_a$ independently represents lower alkyl;

Ar is phenyl, 1- or 2-naphthyl, 2-, 3-, or 4-pyridyl, 2-, 4- or 5-pyrimidinyl, optionally mono-, di-, or tri-substituted with halogen, trifluoromethyl, hydroxy, amino, lower alkylamino, lower dialkylamino, carboxamido, lower alkylcarboxamido, N,N-lower dialkylcarboxamido, lower alkyl, lower alkoxy, with the proviso that at least one of the positions ortho or para to the point of attachment of Ar to the tricyclic ring system is substituted;

$R^1$ is hydrogen, halogen, trifluoromethyl, lower alkyl, or ($C_1$–$C_6$ alkyl)-$G^1$—$R^2$ where $G^1$ is oxygen or sulfur and $R^2$ is hydrogen or $C_1$–$C_6$ alkyl;

W is N or C—$R^3$ where $R^3$ is hydrogen or lower alkyl;

$Q^1$ is hydrogen, lower alkyl, halogen, lower alkoxy, amino, methylamino, dimethylamino, hydroxymethyl, or $SO_n$($C_1$–$C_4$ alkyl) where n is 0, 1 or 2, cyano, hydroxy, —C(O)($C_1$–$C_4$ alkyl), —CHO, —$CO_2$($C_1$–$C_4$ alkyl), —$CO_2$($C_1$–$C_4$ alkenyl), or —$CO_2$ ($C_1$–$C_4$ alkynyl);

$Q^2$ is hydrogen, lower alkyl, halogen, hydroxymethyl, methoxymethyl, or lower alkoxy;

X is

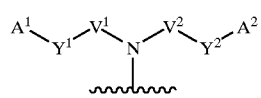 (i)

wherein $V^1$ and $V^2$ are $CH_2$, CO, CS, $SO_2$ or CH(lower alkyl), with the proviso that both $V^1$ and $V^2$ cannot both be CO, CS or $SO_2$;

$Y^1$ and $Y^2$ independently represent a bond or lower alkylene;

$A^1$ is $NR^4R^5$ wherein $R^4$ and $R^5$ are independently hydrogen or a lower alkyl group which optionally forms a heterocycloalkyl group with $Y^1$;

lower alkanoyl, lower alkylsulfonyl, with the proviso that $R^4$ and $R^5$ cannot both be alkanoyl or alkylsulfonyl; or $NR^4R^5$ taken together form a $C_3$–$C_6$ heterocycloalkyl or a group of the formula:

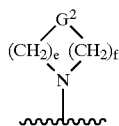

wherein e and f are independently 1, 2 or 3 and the sum of e and f is at least 3; and $G^2$ is $NR^6$ wherein $R^6$ is hydrogen or lower alkyl, or CH($C_0$–$C_6$ alkylene)-$G^3$—$R^7$ wherein $G^3$ is CONH, CONH(lower alkyl), NH, NH(lower alkyl) and $R^7$ is hydrogen or lower alkyl; or $CONH_2$, CO[N(lower alkyl)$R^8$] wherein $R^8$ is hydrogen or lower alkyl;

$A^2$ is hydrogen, lower alkyl, ($C_1$–$C_6$ alkylene)-$G^4$—$R^9$ wherein $G^4$ is oxygen or sulfur and $R^9$ is hydrogen, trifluoromethyl or lower alkyl;

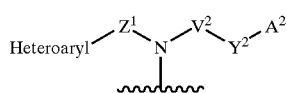 (ii)

wherein heteroaryl is 2-, 3- or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono- or disubstituted with halogen, trifluoromethyl, amino, lower alkyl, lower alkoxy, with the proviso that tetrazolyl can have at most one substituent;

$Z^1$ is lower alkyl; and $V^2$, $Y^2$ and $A^2$ are as defined above;

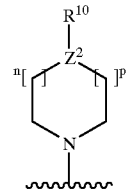 (iii)

where $Z^2$ is carbon or nitrogen;
where
is when $Z^2$ is CH, n is 0, 1, 2 or 3 and p is 1, 2, or 3, $R^{10}$ is carboxamido, or (lower alkylene)-$G^5$—$R^{11}$ wherein $G^5$ is NH, NH(lower alkyl) and $R^{11}$ is hydrogen or lower alkyl;

when $Z^2$ is carbon, n is 1 or 2 and p is 1 or 2, $R^{10}$ is amino; or when $Z^2$ is nitrogen, n is 1 or 2 and p is 1 or 2, $R^{10}$ is hydrogen; or (iv) a nitrogen heterocycle of the formula:

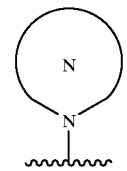

wherein the N-ring represents triazolyl, tetrazolyl, imidazolyl, or pyrazolyl, each of which is optionally substituted with amino, trifluoromethyl, carboxamido, or (lower alkylene)-$G^6$—$R^{12}$ wherein $G^6$ is NH, NH(lower alkyl) and $R^{12}$ is hydrogen or lower alkyl.

In Formula III, $Q^1$ and $Q^2$ preferably independently represent hydrogen, methyl, or ethyl. Particularly preferred compounds of Formula III are those where N—$V^2$—$Y^2$—$A^2$ represents N-cyclopropylmethyl. Other more preferred compounds of Formula III include those where one of $Q^1$ and $Q^2$ is methyl or ethyl and the other is hydrogen.

Still other more preferred compounds of Formula III are those where N—$V^2$—$Y^2$—$A^2$ represents N-cyclopropylmethyl, $Q^1$ is methyl or ethyl, and —$V^1$—$Y^1$—$A^1$ represents

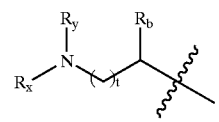

hereinafter Formula III-a,
wherein
$R_b$ is hydrogen or methyl;
t is 1, 2 or 3, more preferably 1;
$R_x$ is hydrogen, $C_1$–$C_6$ alkyl, phenyl($C_1$–$C_6$)alkyl where phenyl is optionally mono- or disubstituted independently with $C_1$–$C_6$ alkyl, $C_1$–$C_6$ alkoxy, halogen, or hydroxy; and
$R_y$ is hydrogen, $C_1$–$C_6$ alkyl, ($C_3$–$C_6$)cycloalkyl; or $NR_xR_y$ represents pyrrolidinyl, N-($C_1$–$C_6$) alkylpyrrolidin-2-yl, piperidinyl, morpholinyl, or N-($C_1$–$C_6$)alkylpiperazinyl.

Particularly preferred compounds of Formula III include those where N—V²—Y²—A² represents N-cyclopropylmethyl, Q¹ is methyl, and —V¹—Y¹—A¹ represents III-a where $R_b$ is hydrogen, and t is 1. Particularly preferred $R_x$ and $R_y$ groups are independently hydrogen or $C_1$–$C_2$ alkyl, or where $NR_xR_y$ represents pyrrolidinyl, piperidinyl or piperazinyl.

Preferred compounds of the invention include the following:

4-(N-(2-Pyrrolidinyl)ethyl-N-cyclopropylmethyl)amino-3,6-dimethyl-1-(2,4,6-trimethylphenyl)pyrrolo[2,3-b]pyridine 4-(N-(2-Pyrrolidinyl)ethyl-N-cyclopropylmethyl)amino-2,5-dimethyl-7-(2,4,6-trimethylphenyl)pyrrolo[3,2-e]pyrimidine 4-(N-(2-Piperidinyl)ethyl-N-cyclopropylmethyl)amino-3,6-dimethyl-1-(2,4,6-trimethylphenyl)pyrrolo[2,3-b]pyridine 4-(N-(2-Morpholinyl)ethyl-N-cyclopropylmethyl)amino-3,6-dimethyl-1-(2,4,6-trimethylphenyl)pyrrolo[2,3-b]pyridine 4-(N-(2-Piperazinyl)ethyl-N-cyclopropylmethyl)amino-3,6-dimethyl-1-(2,4,6-trimethylphenyl)pyrrolo[2,3-b]pyridine 4-(N-(2-Morpholinyl)ethyl-N-cyclopropylmethyl)amino-3,6-dimethyl-1-(2,4,6-trimethylphenyl)pyrrolo[2,3-b]pyrimidine 4-(N-(2-Piperazinyl)ethyl-N-cyclopropylmethyl)amino-3,6-dimethyl-1-(2,4,6-trimethylphenyl)pyrrolo[2,3-b]pyrimidine 4-(N-(2-Methylamino)ethyl-N-cyclopropylmethyl)amino-2,5-dimethyl-7-(2,4,6-trimethylphenyl)pyrrolo[3,2-e]pyrimidine 4-(N-(2-Dimethylamino)ethyl-N-cyclopropylmethyl)amino-2,5-dimethyl-7-(2,4,6-trimethylphenyl)pyrrolo[3,2-e]pyrimidine 4-(N-(2-Ethylmethylamino)ethyl-N-cyclopropylmethyl)-amino-2,5-dimethyl-7-(2,4,6-trimethylphenyl)pyrrolo[3,2-e]pyrimidine 4-(N-(2-Ethylamino)ethyl-N-cyclopropylmethyl)amino-2,5-dimethyl-7-(2,4,6-trimethylphenyl)pyrrolo[3,2-e]pyrimidine 4-(N-(2-Diethylamino)ethyl-N-cyclopropylmethyl)amino-2,5-dimethyl-7-(2,4,6-trimethylphenyl)pyrrolo[3,2-e]pyrimidine 4-(N-(2-Piperazinyl)ethyl-N-cyclopropylmethyl)amino-3,6-dimethyl-1-(2,4,6-trimethylphenyl)pyrrolo[2,3-b]pyridine 4-(N-(2-(4-Methylpiperazinyl))ethyl-N-cyclopropylmethyl)amino-3,6-dimethyl-1-(2,4,6-trimethylphenyl)pyrrolo[2,3-b]pyridine In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH₂)n—ACOOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By "alkyl", "lower alkyl", or $C_1$–$C_6$ alkyl in the present invention is meant straight or branched chain alkyl groups having 1–6 carbon atoms optionally forming a 3 to 6 atoms carbocycle, such as, for example, methyl, ethyl, propyl, isopropyl, cyclopropyl, cyclopropylmethyl, n-butyl, sec-butyl, tert-butyl, cyclobutyl, pentyl, 2-pentyl, isopentyl, neopentyl, cyclopentyl, hexyl, 2-hexyl, 3-hexyl, 3-methylpentyl, cyclohexyl.

By $C_0$–$C_6$ alkylene is meant a direct bond or a $C_1$–$C_6$ alkylene group, optionally forming a 3 to 6 atoms carbocycle, such as methylene, ethylidene, propylidene, butylidene, pentylidene, cyclopentylidene, hexylidene, cyclohexylidene.

By "alkoxy", "lower alkoxy", or $C_1$–$C_6$ alkoxy in the present invention is meant straight or branched chain alkoxy groups having 1–6 carbon atoms optionally forming a 3 to 6 atoms carbocycle, such as, for example, methoxy, ethoxy, propoxy, isopropoxy, cyclopropylmethoxy, n-butoxy, sec-butoxy, tert-butoxy, pentoxy, 2-pentoxy, isopentoxy, neopentoxy, cyclopentoxy, hexoxy, 2-hexoxy, 3-hexoxy, 3-methylpentoxy, cyclohexoxy.

By "alkanoyl", "lower alkanoyl", or $C_1$–$C_6$ alkanoyl in the present invention is meant straight or branched chain alkanoyl groups having 1–6 carbon atoms optionally forming a 3 to 6 atoms carbocycle, such as, for example, acetyl, propionyl, isopropionyl, cyclopropionyl, butanoyl, pentanoyl, cyclopentanoyl, hexanoyl, cyclhexanoyl.

CONH represents an amide functional group, i.e.,

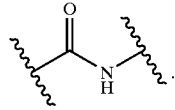

The term "heterocycle" or "heterocycloalkyl" means a monocyclic or bicyclic hydrocarbon group which in which one or more of the ring carbon atoms has been replaced with a heteroatom, e.g., oxygen, sulfur or nitrogen. Such groups preferably have 4 to 10 carbon atoms and 1 to 4 heteroatoms.

By the term "halogen" in the present invention is meant fluorine, bromine, chlorine, and iodine.

The interaction of aminoalkyl substituted pyrrolo[3,2-e]pyridine and pyrrolo[2,3-b]pyrimidine derivatives of the invention with $CRF_1$ receptors is shown in the examples below. This interaction results in the pharmacological activities of these compounds as illustrated in relevant animal models.

As the compounds of Formula I are effective $CRF_1$ receptor antagonists, they are useful for the treatment of psychiatric disorders, neurological diseases, immunological, cardiovascular or heart-related diseases and colonic hypersensitivity associated with psychopathological disturbance and stress.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachid oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachid oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preparation of Aminoalkyl Substituted Pyrrolo[3,2-e]pyridine and Pyrrolo[2,3-b]pyrimidine Analogues An illustration of the preparation of compounds of the present invention is given in Scheme I, Scheme II and Scheme III. Those having skill in the art will recognize that the starting materials may be varied and additional steps employed to produce compounds encompassed by the present invention.

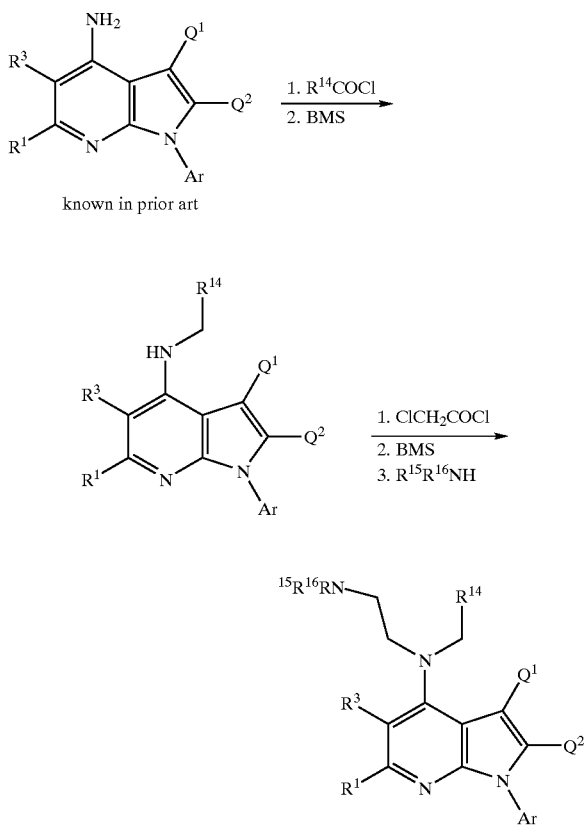

wherein Ar, $Q^1$, $Q^2$, $R^1$ and $R^3$ are as defined above for Formula I; and $R^{14}$, $R^{15}$ and $R^{16}$ are encompassed by the definition of X for Formula I.

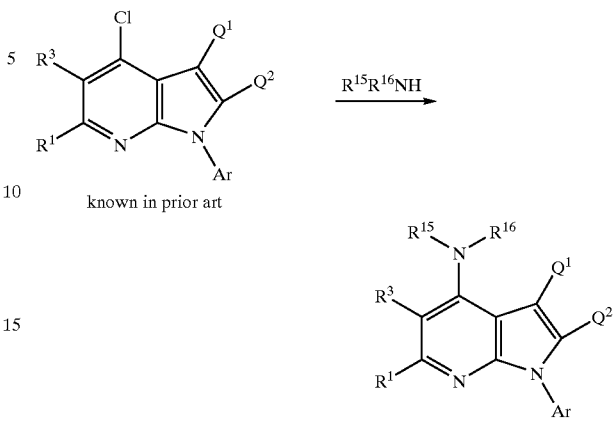

wherein Ar, $Q^1$, $Q^2$, $R^1$ and $R^3$ are as defined above for Formula I; and $R^{15}$ and $R^{16}$ are encompassed by the definition of X for Formula I.

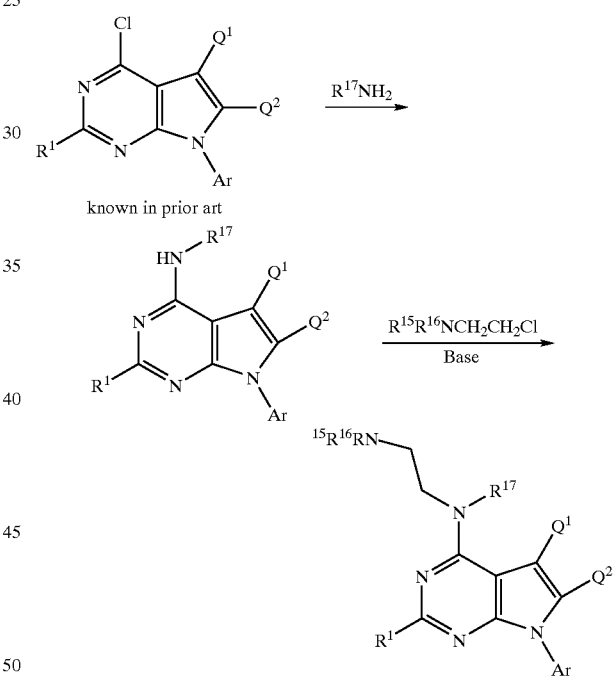

wherein Ar, $Q^1$, $Q^2$ and $R^1$ are as defined above for Formula I; and $R^{15}$, $R^{16}$ and $R^{17}$ are encompassed by the definition of X for Formula I.

The disclosures of all articles and references mentioned in this application, including patents, are incorporated herein by reference.

The preparation of the compounds of the present invention is illustrated further by the following Examples, which are not to be construed as limiting the invention in scope or spirit to the specific procedures and compounds described in them.

Commercial reagents are used without further purification. THF refers to tetrahydrofuran. Room or ambient temperature refers to 20 to 25° C. Concentration implies the use of a rotary evaporator. TLC refers to thin layer chromatography. Mass spectral data are obtained either by CI or APCI methods.

EXAMPLE 1

A. 4-(N-Cyclopropylmethyl)amino-3,6-dimethyl-1-(2,4,6-trimethylphenyl)pyrrolo[2,3-b]pyridine

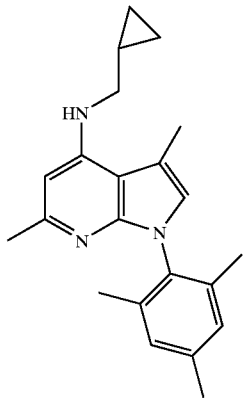

A solution of dichloroethane (70 mL) containing 4-amino-3,6-dimethyl-1-(2,4,6-trimethylphenyl)pyrrolo[2,3-b]pyridine (11 g) and cyclopropanecarbonyl chloride (3.4 mL) at reflux is treated with dropwise addition of N,N-diisopropylethylamine (6.6 mL). After heating for 0.5 hour the reaction is cooled to ambient temperature and poured into aqueous potassium carbonate solution. The product is extracted with dichloromethane, dried over sodium sulfate, filtered and concentrated. The concentrate is re-dissolved in THF (100 mL) and mixed with borane-methyl sulfide complex (10M, 10.3 mL). The mixture is heated to reflux for 8 hours and quenched at room temperature with a large excess of methanol (about 100 mL). Re-heat mixture to reflux for 1 hour, then concentrate under reduced pressure. More methanol (another 50 mL) is added to the gummy residue and the solution is re-concentrated to yield a white solid.

B. 4-(N-(2-Chloroethyl)-N-cyclopropylmethyl)amino-3,6dimethyl-1-(2,4,6-trimethylphenyl)pyrrolo[2,3-b]pyridine

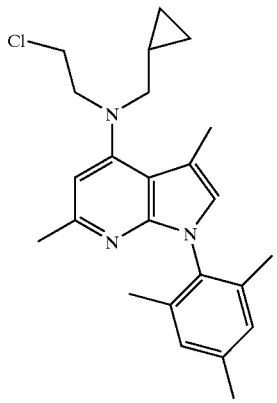

A solution containing the product from Example 1A (13 g) and chloroacetyl chloride (3 mL) in dichloroethane (100 mL) is refluxed for 4 hours. The solvent and excess reagent are removed under reduced pressure. Aqueous potassium carbonate is added to the remaining oily residue and extracted with dichloromethane. The extract is dried with sodium sulfate, filtered and concentrated. The latter chloroacetyl compound (15 g) is dissolved in THF (100 mL). Add borane-methyl sulfide complex (10M, 3.4 mL) and stir at ambient temperature for 15 minutes then for 1 hour at reflux temperature. The solution is cooled back to room temperature, quenched with a large excess of methanol (50 mL) and re-heated to reflux for 1 hour. The solution is then concentrated.

C. 4-(N-(2-Dimethylamino)ethyl-N-cyclopropylmethyl)-amino-3,6-dimethyl-1-(2,4,6-trimethylphenyl)pyrrolo2,3-b]pyridine (Compound 1)

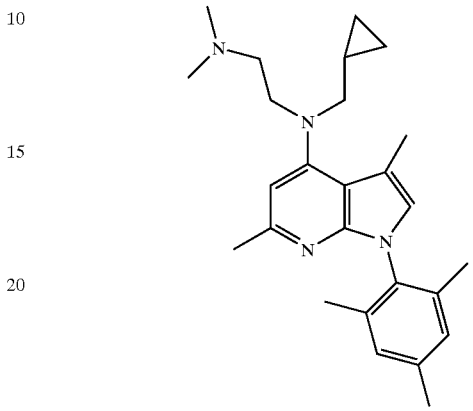

A steel bomb containing the product from Example 1B (3.8 g), dimethylamine (8 mL) and N-methylpyrrolidinone (20 mL) is sealed and heated to 80° C. for 10 hours. The mixture is poured into water and extracted with ethyl acetate. The organic layer is washed with water, dried over sodium sulfate, filtered and concentrated.

EXAMPLE 2

The following compounds are prepared essentially according to the procedures set forth in Example 1 and/or Schemes I, II, and III.

a) 4-(N-(2-Methylamino)ethyl-N-cyclopropylmethyl) amino-3,6-dimethyl-1-(2,4,6-trimethylphenyl)pyrrolo[2,3-b]pyridine (Compound 2)

b) 4-(N-(2-Pyrrolidinyl)ethyl-N-cyclopropylmethyl)amino-3,6-dimethyl-1-(2,4,6-trimethylphenyl)pyrrolo[2,3-b]pyridine (Compound 3)

c) 4-(N-(2-Ethylmethylamino)ethyl-N-cyclopropylmethyl)-amino-3,6-dimethyl-1-(2,4,6-trimethylphenyl)pyrrolo[2,3-b]pyridine (Compound 4)

d) 4-(N-(2-Ethylamino)ethyl-N-cyclopropylmethyl)amino-3,6-dimethyl-1-(2,4,6-trimethylphenyl)pyrrolo[2,3-b]pyridine (Compound 5)

e) 4-(N-(2-Diethylamino)ethyl-N-cyclopropylmethyl) amino-3,6-dimethyl-1-(2,4,6-trimethylphenyl)pyrrolo[2,3-b]pyridine (Compound6)

f) 4-(N-(2-Piperidinyl)ethyl-N-cyclopropylmethyl)amino-3,6-dimethyl-1-(2,4,6-trimethylphenyl)pyrrolo[2,3-b]pyridine (Compound 7)

g) 4-(N-(2-Morpholinyl)ethyl-N-cyclopropylmethyl)amino-3,6-dimethyl-1-(2,4,6-trimethylphenyl)pyrrolo[2,3-b]pyridine (Compound 8)

h) 4-(N-(2-Piperazinyl)ethyl-N-cyclopropylmethyl)amino-3,6-dimethyl-1-(2,4,6-trimethylphenyl)pyrrolo[2,3-b]pyridine (Compound 9)

i) 4-(N-(2-(4-Methylpiperazinyl))ethyl-N-cyclopropylmethyl)amino-3,6-dimethyl-1-(2,4,6-trimethylphenyl)pyrrolo[2,3-b]pyridine (Compound 10)

EXAMPLE 3

4-(N-(2-Aminoethyl)-N-cyclopropylmethyl)amino-3,6-dimethyl-1-(2,4,6-trimethylphenyl)pyrrolo[2,3-b]pyridine (Compound 11)

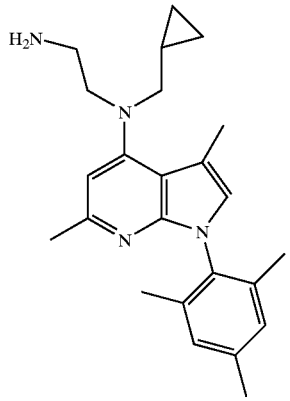

A solution containing the product from Example 1B (500 mg) and sodium azide (22 mg) in N-methylpyrrolidinone (5 mL) is heated to 120° C. for 2 hours. The mixture is poured into water and extracted with ethyl acetate. The organic layer is washed with water, dried over sodium sulfate, filtered and concentrated. An ethanol (10 mL) solution of the crude product and 10% palladium on carbon (about 200 mg) is hydrogenated for 8 hours at approximately 1 atmosphere pressure. The suspension is filtered over celite and concentrated.

EXAMPLE 4

A. 4-Chloro-3,6-dimethyl-1-(2,4,6-trimethylphenyl)pyrrolo[2,3-b]pyridine

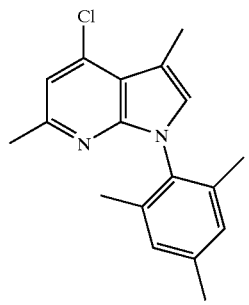

Dissolve tert-butylnitrite (0.65 g) in acetonitrile (10 mL) and add copper(II)chloride (0.68 g). Then 4-amino-3,6-dimethyl-1-(2,4,6-trimethylphenyl)pyrrolo[2,3-b]pyridine (1.33 g) is added portionwise to the greenish-brown solution and the mixture is stirred for 12 hours. The acetonitrile is removed by evaporation and the residue is partitioned between water and dichloromethane. The aqueous layer is extracted with more dichloromethane and the combined extract is washed with water, dried over sodium sulfate, filtered and concentrated.

B. 4-Piperazinyl-3,6-dimethyl-1-(2,4,6-trimethylphenyl)pyrrolo[2,3-b]pyridine (Compound 12)

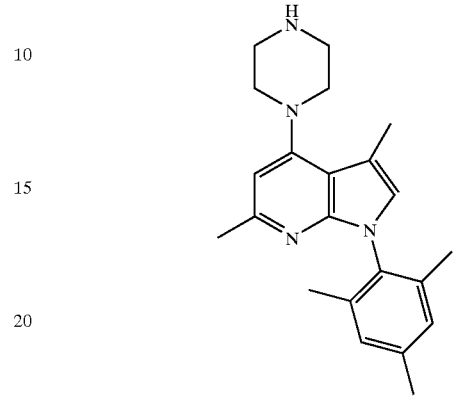

Combine the compound from Example 4A (200 mg) and piperazine (0.58 g) in N-methylpyrrolidinone (2 mL) and heat the solution to 120° C. for 12 hours. Pour mixture into water and extract with ethyl acetate. Wash extract with aqueous ammonium chloride then water. Dry extract over sodium sulfate, filter and concentrate.

EXAMPLE 5

A. 4-(N-Cyclopropylmethyl)amino-2,5-dimethyl-7-(2,4,6-trimethylphenyl)pyrrolo[3,2-e]pyrimidine

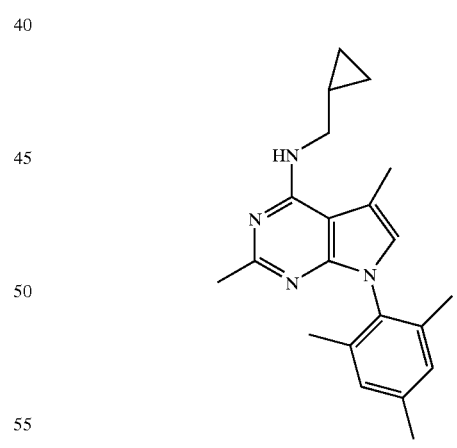

A mixture containing 4-chloro-2,5-dimethyl-7-(2,4,6-trimethylphenyl)pyrrolo[3,2-e]pyrimidine (450 mg), cyclopropylmethylamine hydrochloride (800 mg) and triethylamine (1.3 mL) in N-methylpyrrolidinone (3 mL) is heated to 110° C. in a sealed tube for 4 hours. Dilute mixture with ethyl acetate and wash with water, aqueous ammonium chloride and brine. Dry over sodium sulfate, filter and concentrate to give a tan colored solid: MS 335 (M+H).

B. 4-(N-(2-Pyrrolidinyl)ethyl-N-cyclopropylmethyl)-amino-2,5-dimethyl-7-(2,4,6-trimethylphenyl)pyrrolo[3,2e]pyrimidine (Compound 13)

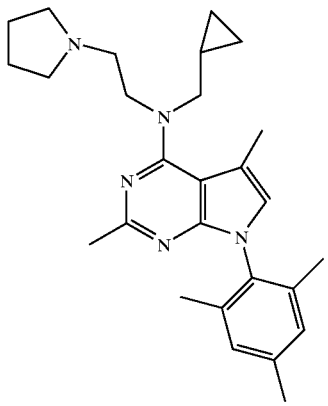

To a solution of the compound from Example 5A (130 mg) in N,N-dimethylformamide (1 mL) at 0° C., under a blanket of nitrogen, is added sodium hydride (60%, 70 mg). After stirring the solution for 0.5 hours, 2-dimethylaminoethyl chloride hydrochloride (135 mg) is added. The mixture is then heated to 40° C. for 2 hours, then quenched with ice and water. Dilute with ethyl acetate and wash with water, brine, dry over sodium sulfate, filter and concentrate. Purify by preparative TLC using 10% methanol and 0.5% ammonium hydroxide in dichloromethane as eluent to obtain 100 mg of product: MS 432 (M+H).

EXAMPLE 6

The following compounds are prepared essentially according to the procedures set forth in Example 5 and/or Schemes I, II, and III.
a) 4-(N-(2-Methylamino)ethyl-N-cyclopropylmethyl)amino-2,5-dimethyl-7-(2,4,6-trimethylphenyl)pyrrolo[3,2-e]pyrimidine (Compound 14)
b) 4-(N-(2-Dimethylamino)ethyl-N-cyclopropylmethyl)amino-2,5-dimethyl-7-(2,4,6-trimethylphenyl)pyrrolo[3,2-e]pyrimidine (Compound 15)
c) 4-(N-(2-Ethylmethylamino)ethyl-N-cyclopropylmethyl)-amino-2,5-dimethyl-7-(2,4,6-trimethylphenyl)pyrrolo[3,2-e]pyrimidine (Compound 16)
d) 4-(N-(2-Ethylamino)ethyl-N-cyclopropylmethyl)amino-2,5-dimethyl-7-(2,4,6-trimethylphenyl)pyrrolo[3,2-e]pyrimidine (Compound 17)
e) 4-(N-(2-Diethylamino)ethyl-N-cyclopropylmethyl)amino-2,5-dimethyl-7-(2,4,6-trimethylphenyl)pyrrolo[3,2-e]pyrimidine (Compound 18)
f) 4-(N-(2-Piperidinyl)ethyl-N-cyclopropylmethyl)amino-2,5-dimethyl-7-(2,4,6-trimethylphenyl)pyrrolo[3,2-e]pyrimidine (Compound 19)
g) 4-(N-(2-Morpholinyl)ethyl-N-cyclopropylmethyl)amino-2,5-dimethyl-7-(2,4,6-trimethylphenyl)pyrrolo[3,2-e]pyrimidine (Compound 20)
h) 4-(N-(2-Piperazinyl)ethyl-N-cyclopropylmethyl)amino-2,5-dimethyl-7-(2,4,6-trimethylphenyl)pyrrolo[3,2-e]pyrimidine (Compound 21)
i) 4-(N-(2-(4-Methylpiperazinyl))ethyl-N-cyclopropylmethyl)amino-2,5-dimethyl-7-(2,4,6-trimethylphenyl)pyrrolo[3,2-e]pyrimidine (Compound 22)

EXAMPLE 7

The pharmaceutical utility of compounds of this invention are indicated by the following assays for human $CRF_1$ receptor activity.

Assay for Recombinant Human $CRF_1$ Receptor Binding Activity

CRF receptor binding is performed using a modified version of the assay described by Grigoriadis and De Souza (*Methods in Neurosciences, Vol. 5*, 1991). Membrane pellets containing CRF receptors are re-suspended in 50 mM Tris buffer pH 7.7 containing 10 mM $MgCl_2$ and 2 mM EDTA and centrifuged for 10 minutes at 48000 g. Membranes are washed again and brought to a final concentration of 1500 mg/ml in binding buffer (Tris buffer above with 0.1% BSA, 15 mM bacitracin and 0.01 mg/mL aprotinin.). For the binding assay, 100 mL of the membrane preparation is added to 96 well microtube plates containing 100 mL of $^{125}$I-CRF (SA 2200 Ci/mmol, final concentration of 100 pM) and 50 mL of drug. Binding is carried out at room temperature for 2 hours. Plates are then harvested on a Brandel 96 well cell harvester and filters are counted for gamma emissions on a Wallac 1205 Betaplate liquid scintillation counter. Non specific binding is defined by 1 mM cold CRF. $IC_{50}$ values are calculated with the non-linear curve fitting program RS/1 (BBN Software Products Corp., Cambridge, Mass). The binding affinity for the compounds of Formula I expressed as $IC_{50}$ value, generally ranges from about 0.5 nanomolar to about 10 micromolar.

Alternatively, the binding activity of the compounds of formula I to the human $CRF_1$ receptor can be measured as follows:

Assay for Human CRF Receptor Binding Activity in IMR32 Cells

[$^{125}$I]Sauvagine Binding to $CRF_1$ Receptors Endogenously Expressed in IMR-32 Cells: IMR-32 human neuroblastoma cells are grown to 80% confluence in EMEM containing Earle's Balanced Salts and 2 mM 1-glutamine with 10% FBS, 25 mM HEPES, 1 mM Sodium Pyruvate, and nonessential amino acids. At this time, flasks of cells are treated with 2.5 μM 5-bromo-2'-deoxyuridine (Br-dU) for 10 days. Media is changed every 3–4 days across the 10 day period. Cells are harvested using No-Zyme (JRH Biosciences) and rinsed with PBS. For membrane preparation, cells are homogenized in wash buffer (50 mM Tris HCl, 10 mM $MgCl_2$, 2 mM EGTA, pH 7.4) and centrifuged at 48,000×g for 10 minutes at 4° C. Pellets are re-suspended, homogenized and centrifuged two additional times. The receptor binding assay is performed using assay buffer (50 mM Tris HCl, 10 mM $MgCl_2$, 2 mM EGTA, pH 7.4, 0.1% BSA, 0.1 mM bacitracin (22.0 mg/100 mL)), 150 μg protein/tube, and [$^{125}$I]Sauvagine (NEN; 100 pM for competition analysis and 10 pM-1 nM for saturation analysis) to yield a final volume of 200 uL. Nonspecific binding is defined using 2 μM r/h CRF or 9-41 alpha-helical CRF. Cells are incubated for 2 hours at room temperature. The assay is terminated by rapid vacuum filtration (Tomtec: Deepwell 3) through GFC filters presoaked in 1% PEI using ice-cold 50 mM Tris HCl and dry thoroughly by air. Specific Binding: 70–80%; Kd (nM): 0.30 nM; Bmax (fmole/mg protein): 40–50. $IC_{50}$ values are calculated with the non-linear curve fitting program RS/1 (BBN Software Products Corp., Cambridge, Mass.).

The binding affinity for the compounds of Formula I expressed as $IC_{50}$ value, generally ranges from about 0.5 nanomolar to about 10 micromolar.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

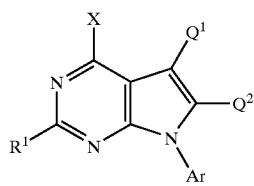

or a pharmaceutically acceptable salt thereof wherein

Ar is phenyl, 1- or 2-naphthyl, 2-, 3-, or 4-pyridyl, 2-, 4- or 5-pyrimidinyl, optionally mono-, di-, or tri-substituted with halogen, trifluoromethyl, hydroxy, amino, lower alkylamino, lower dialkylamino, carboxamido, lower alkylcarboxamido, N,N-lower dialkylcarboxamido, lower alkyl, lower alkoxy, with the proviso that at least one of the positions ortho or para to the point of attachment of Ar to the bicyclic ring system is substituted;

$R^1$ is hydrogen, halogen, trifluoromethyl, lower alkyl, or $(C_1-C_6$ alkyl$)$-$G^1$—$R^2$ where $G^1$ is oxygen or sulfur and $R^2$ is hydrogen or $C_1$–$C_6$ alkyl;

$Q^1$ is hydrogen, lower alkyl, halogen, lower alkoxy, amino, methylamino, dimethylamino, hydroxymethyl, or $SO_n(C_1$–$C_4$ alkyl) where n is 0, 1 or 2, cyano, hydroxy, —C(O) ($C_1$–$C_4$ alkyl), —CHO, —$CO_2$ ($C_1$–$C_4$ alkyl), —$CO_2(C_1$–$C_4$ alkenyl), or —$CO_2$ ($C_1$–$C_4$ alkynyl);

$Q^2$ is hydrogen, lower alkyl, halogen, hydroxymethyl, methoxymethyl, or lower alkoxy; and X is a group of the formula

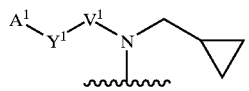

wherein $V^1$ is $CH_2$ or CH(lower alkyl);

$Y^1$ represents a bond or lower alkylene;

$A^1$ is $NR^4R^5$ wherein $R^4$ and $R^5$ are independently lower alkyl; or $A^1$ is $NR^4R^5$ wherein $R^4$ and $R^5$ are taken together to form a morpholinyl, piperazinyl, piperidinyl, or pyrrolidinyl group.

2. A compound according to claim 1, wherein $Q^1$ and $Q^2$ are independently methyl or ethyl.

3. A compound according to claim 1, wherein $Q^1$ is methyl, $Q^2$ is hydrogen or methyl, $R^1$ is methyl, Ar is 2,4,6-trimethylphenyl, and X is (N-(2-pyrrolidinyl)ethyl-N-cyclopropylmethyl)amino or (N-(2-dimethylamino)ethyl-N-cyclopropylmethyl)amino.

4. A compound of the formula

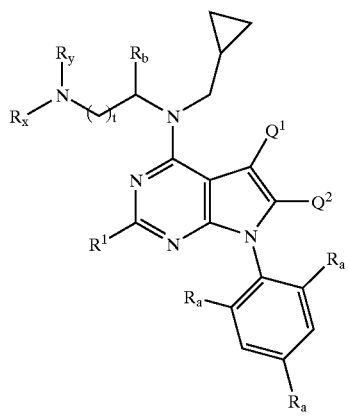

or a pharmaceutically acceptable salt thereof, wherein each $R_a$ is independently lower alkyl;

$R_b$ is hydrogen or methyl;

t is 1, 2, or 3;

$R_x$ is hydrogen, $C_1$–$C_6$alkyl, phenyl $(C_1$–$C_6)$alkyl where phenyl is optionally mono- or disubstituted independently with $C_1$–$C_6$ alkyl, $C_1$–$C_6$alkoxy, halogen, or hydroxy; and $R_y$ is hydrogen, $C_1$–$C_6$ alkyl, $(C_3$–$C_6)$cycloalkyl; or $NR_xR_y$ represents pyrrolidinyl, N-$(C_1$–$C_6)$ alkylpyrrolidin-2-yl, piperidinyl, morpholinyl, or N-$(C_1$–$C_6)$alkylpiperazinyl;

$Q^1$ and $Q^2$ independently represent hydrogen, methyl, or ethyl; and $R^1$ is hydrogen, halogen, trifluoromethyl, lower alkyl, or $(C_1$–$C_6$ alkyl$)$-$G^1$—$R^2$ where $G^1$ is oxygen or sulfur and $R^2$ is hydrogen or $C_1$–$C_6$ alkyl.

5. A compound or salt according to claim 1 which is 4-(N-(2-Pyrrolidinyl)ethyl-N-cyclopropylmethyl)amino-2,5-dimethyl-7-(2,4,6-trimethylphenyl)pyrrolo[3,2-e]pyrimidine.

6. A compound or salt according to claim 1 which is 4-(N-(2-Methylamino)ethyl-N-cyclopropylmethyl)amino-2,5-dimethyl-7-(2,4,6-trimethylphenyl)pyrrolo[3,2-e]pyrimidine.

7. A compound or salt according to claim 1 which is 4-(N-(2-Dimethylamino)ethyl-N-cyclopropylmethyl)amino-2,5-dimethyl-7-(2,4,6-trimethylphenyl)pyrrolo[3,2-e]pyrimidine.

8. A compound or salt according to claim 1 which is 4-(N-(2-Ethylmethylamino)ethyl-N-cyclopropylmethyl)amino-2,5-dimethyl-7-(2,4,6-trimethylphenyl)pyrrolo[3,2-e]pyrimidine.

9. A compound or salt according to claim 1, which is 4-(N-(2-Ethylamino)ethyl-N-cyclopropylmethyl)amino-2,5-dimethyl-7-(2,4,6-trimethylphenyl)pyrrolo[3,2-e]pyrimidine.

10. A compound or salt according to claim 1 which is 4-(N-(2-Diethylamino)ethyl-N-cyclopropylmethyl)amino-2,5-dimethyl-7-(2,4,6-trimethylphenyl)pyrrolo[3,2-e]pyrimidine.

11. A compound or salt according to claim 1 which is 4-(N-Cyclopropylmethyl)amino-2,5-dimethyl-7-(2,4,6-trimethylphenyl)pyrrolo[3,2-e]pyrimidine.

12. A compound or salt according to claim 1 which is 4-(N-(2-Pyrrolidinyl)ethyl-N-cyclopropylmethyl)amino-2,5-dimethyl-7-(2,4,6-trimethylphenyl)pyrrolo[3,2-e]pyrimidine.

13. A compound or salt according to claim 10 which is 4-(N-(2-Piperidinyl)ethyl-N-cyclopropylmethyl)amino-2,5-dimethyl-7-(2,4,6-trimethylphenyl)pyrrolo[3,2-e]pyrimidine.

14. A compound or salt according to claim 1 which is 4-(N-(2-Morpholinyl)ethyl-N-cyclopropylmethyl)amino-2,5-dimethyl-7-(2,4,6-trimethylphenyl)pyrrolo[3,2-e]pyrimidine.

15. A compound or salt according to claim 1 which is 4-(N-(2-Piperazinyl)ethyl-N-cyclopropylmethyl)amino-2,5-dimethyl-7-(2,4,6-trimethylphenyl)pyrrolo[3,2-e]pyrimidine.

16. A compound or salt according to claim 1 which is 4-(N-(2-(4-Methylpiperazinyl))ethyl-N-cyclopropylmethyl)amino-2,5-dimethyl-7-(2,4,6-trimethylphenyl)pyrrolo[3,2-e]pyrimidine.

17. A pharmaceutical composition comprising a pharmaceutically acceptable carrier and a compound of claim 1.

18. A method of treating anxiety, depression, or post-traumatic stress disorder comprising administering a therapeutically effective amount of a compound of claim 1 to a patient in need thereof.

* * * * *